US006514396B1

United States Patent
Yarnitzky

(10) Patent No.: US 6,514,396 B1
(45) Date of Patent: Feb. 4, 2003

(54) DROPPING MERCURY ELECTRODE WITH MERCURY PURIFICATION AND RECYCLING BY MEANS OF CONTACT WITH OXYGENATED WATER

(76) Inventor: Chaim Noah Yarnitzky, 11 Orca Street, 34731 Haifa (IL)

( * ) Notice: Subject to any disclaimer, the term of this patent is extended or adjusted under 35 U.S.C. 154(b) by 0 days.

(21) Appl. No.: 09/583,330

(22) Filed: May 31, 2000

Related U.S. Application Data

(63) Continuation of application No. PCT/IL98/00583, filed on Nov. 30, 1998.

(30) Foreign Application Priority Data

Dec. 1, 1997 (IL) .................................................. 122374

(51) Int. Cl.⁷ .............................................. G01N 27/34
(52) U.S. Cl. ....................................... 204/413; 210/758
(58) Field of Search ........................ 204/413; 210/758, 210/914; 205/775, 789.5

(56) References Cited

U.S. PATENT DOCUMENTS 3,596,893 A * 8/1971 Foliforov et al. ............ 266/148
3,791,797 A * 2/1974 Yuen ............................ 75/742

FOREIGN PATENT DOCUMENTS

| BE | 501520 | | 3/1951 |
| DE | 1153534 | | 8/1963 |
| EP | 0 148 023 A2 | | 7/1985 |
| GB | 941136 | * | 11/1963 |
| WO | WO96/35117 | | 11/1996 |
| WO | WO96/35118 | | 11/1996 |
| WO | WO97/31264 | | 8/1997 |

OTHER PUBLICATIONS

Skoog, Principles of Instrumental Analysis, 3rd Edition, pp. 851–853, 1985.*
Yarnitzky C.N., Analytical Chemistry, vol. 57, No. 9, Aug. 1985, p. 2011–2015.
Jayaratna, H.G. Mercury Thread Electrode Modified with a Hydrophilic Dialysis Polymer, Analytical Chemistry, vol. 66, No. 18, 15, Sep. 1994.
Kissinger (editor) Laboratory Techniques in Electroanalytical Chemistry, Marcel Dekker, inc., pp. 267–287 (1984).
Translation of Belgium 501,520 Document.

* cited by examiner

Primary Examiner—Robert J. Warden, Sr.
Assistant Examiner—Kaj K. Olsen
(74) Attorney, Agent, or Firm—Anderson Kill & Olick; Eugene Lieberstein; Michael N. Meller

(57) ABSTRACT

An electroanalytical apparatus defining a Static Mercury Drop Electrode cell which includes a capillary tube at the end of which is formed mercury drops to constitute the working electrode including a container for continuously receiving and collecting mercury that has formed said working electrode and has become contaminated, a purifying vessel positioned in fixed relationship to the capillary tube, conduit means for continuously transferring mercury into the purifying vessel from the container, means for introducing highly oxygenated water into the purifying vessel at a location above the mercury collected in the vessel such that surface contact is established between said highly oxygenated water and the mercury collected in the purifying vessel, and means for continuously drawing mercury from the purifying vessel and feeding it as purified mercury to the capillary tube.

3 Claims, 3 Drawing Sheets

DROPPING MERCURY ELECTRODE WITH MERCURY PURIFICATION AND RECYCLING BY MEANS OF CONTACT WITH OXYGENATED WATER

This application is a continuation of PCT/IL98/00583 filed Nov. 30, 1998.

FIELD OF THE INVENTION

This invention relates to an improved voltammetric apparatus of the Static Mercury Drop Electrode (hereinafter SMDE) type, in which the mercury is purified and recycled

BACKGROUND OF THE INVENTION

Electrochemical detector and voltammetric cells are known in the art and have been used with success for the analysis of trace elements in the laboratory. Two-electrode and three-electrode cells are known. The three-electrode cell comprises a working electrode, a counter-electrode and a reference electrode which has the function of establishing and maintaining a constant potential relative to the working electrode or the sample solution. In principle, the electrodes may be affected by poisoning due to absorption with resulting passivation and loss of signal. In order to avoid such poisoning, the dropping mercury electrode has been adopted in many such cells.

U.S. Pat. No. 3,922,205 describes the basic structure of a polarographic cell. U.S. Pat. No. 4,138,322 discloses a structure of shielded dropping mercury cathode. U.S. Pat. No. 4,260,467 describes a dropping mercury electrode which comprises a reservoir for liquid mercury, a mercury capillary at the outlet end of which mercury drops are formed, and a valve for selective air-purging passage of mercury from the reservoir to the inlet end of the capillary. An automated polarographic cell is described by C. N. Yarnitzky in Analytical Chemistry, Vol. 57, No. 9, August 1985, p. 2011–2015.

Such cells, however, are not fully satisfactory. In some cases, they include solid electrodes which becomes polluted with time. Others are complicated and unreliable or require a very large volume of the sample solution. In others the mercury feed apparatus is complicated, and mercury has to be replaced once a while.

An improved voltammetric apparatus, free from said drawbacks, is disclosed and claimed in PCT application WO 96/35117. It comprises:

a) a cell body housing, in addition to a reference electrode, a working electrode and, in its lowermost portion, a counter-electrode;

b) means for removing oxygen from the sample solution;

c) means for feeding the sample solution to said deoxygenation means, means for feeding a stream of an inert gas to said deoxygenation means, and means for causing said solution to flow in said deoxygenation means, whereby oxygen is removed therefrom by contact with said inert gas;

d) a means for removing said inert gas from said deoxygenation means after deoxygenation of the sample solution;

e) an inlet for the deoxygenated sample solution provided in said cell body in the space between said working electrode and said counter-electrode;

f) an exit for the sample solution provided in said cell body at a level above said working electrode; and g) vacuum and/or pressure means for causing said sample solution to flow to said exit, to be discharged from the cell above said working electrode, thus assuring that the space between said working electrode and said counter-electrode is constantly filled with said sample solution.

Still, the use of mercury drop electrodes, while beneficial in many respects, involves health and ecological problems, from which even the aforesaid improved voltammetric cell is not free. The operator, who feeds mercury to the cell, comes into contact with it. The mercury, which has formed the drops, collects in a sump, which must be handled to recover it. The mercury drop forms at the lower end of a capillary tube and this latter becomes clogged at comparatively frequent intervals, so that it must be replaced. In order to replace the capillary tube, the mercury must be removed from the mercury reservoir. In all these operations and manipulations, the operator comes, to a greater or smaller extent, into contact with the mercury, which contact is ecologically negative and involves a health hazard. These drawbacks are, of course, common to the mercury drop voltammetric cells of the prior art, and this invention has the purpose of eliminating them in any cell in which they exist.

Further, prior art voltammetric apparatus are not satisfactory for carrying out for anodic stripping techniques. Therein, the mercury drop remains in place for a time from 3 to 15 seconds, depending to the capillary used. While this lifetime of the drop is sufficient for polarography, it is not sufficient for anodic stripping, which requires a much longer drop lifetime, in the order of minutes, e.g. about 2 minutes. Further, prior art apparatus are sensitive to small particles, e.g. in the range of 25 to 100 $\mu$m, which can block the capillary tube.

It is therefore an object of this invention to provide an electroanalytical voltammetric apparatus of the Static Mercury Drop Electrode (SMDE) type, which is free of the said drawbacks.

It is another object of the invention to provide such an apparatus, which comprises means for purifying the mercury in situ and feeding the purified mercury back to the capillary tube which contains it and from which the electrode drops are formed, by means which avoid all manipulation on the operator's part and all contact between him and the mercury.

It is a further object of the invention to provide such an apparatus in which clogging incidents are reduced and which comprises means that enables the use of improved electroanalytic techniques such as anodic stripping techniques.

It is a still further object of the invention to provide such an apparatus in which the capillary tube, at the lower end of which the mercury drop forms, can be replaced, in case of clogging, without the operator's coming into contact with the mercury.

Other objects and advantages of the invention will appear as the description proceeds.

SUMMARY OF THE INVENTION

The electroanalytical voltammetric apparatus according to the invention, comprises, in combination with a SMDE voltammetric cell, means for puriying the mercury and recycling the purified mercury to the capillary tube at the lower end of which the mercury drops are formed.

Said means for purifying the mercury is a means for generating surface contact between the contaminated mercury and water having a high oxygen content. Preferably, the water is saturated or nearly saturated with oxygen or air, and its oxygen content is close to 8 mg/L or higher.

Accordingly, an aspect of this invention is a process for continuously purifying and recycling mercury in an SMDE cell, which comprises continuously bringing contaminated mercury and highly oxygenated water into mutual surface contact, whereby the contaminating metals are oxidized and migrate from the mercury to the water, and continuously feeding the resulting purified mercury to the SMDE cell.

Another aspect of the invention is an apparatus for continuously purifying and recycling mercury in an SMDE cell, which comprises means for continuously bringing contaminated mercury and highly oxygenated water into mutual surface contact, whereby the contaminating metals are oxidized and migrate from the mercury to the water, and means for continuously feeding the resulting purified mercury to the SMDE cell.

Preferably, said puriying apparatus comprises a container hereinafter, the "purification container") for continuously receiving contaminated mercury, said mercury accumulating in said container to form a mass having an upper surface, means for forming a layer of highly oxygenated water in said container above said mercury mass, said layer having a lower surface in contact with said upper surface of said mercury mass, and means for continuously withdrawing purified mercury from said container.

Said highly oxygenated water can be produced in any suitable way. A preferred way of producing it consists in forming a layer of water, e.g. salty water, in surface contact with contaminated mercury, and enriching said layer with oxygen. This may be conveniently done, e.g., by introducing contaminated mercury into a purification container, introducing water above the mercury surface to form a layer, and bubbling through said water layer oxygen or an oxygen containing gas, preferably air. Another way of producing said highly oxygenated water layer is to oxygenate water, e.g., by bubbling through it oxygen or an oxygen containing gas, preferably air, or by mixing a water stream with a stream of oxygen or an oxygen containing gas, preferably air, while said water is out of contact with contaminated mercury, and bringing the resulting, highly oxygenated water into contact with the contaminated mercury. This may be conveniently done, e.g., by continuously introducing contaminated mercury into a purification container, continuously introducing the highly oxygenated water into said purification container above the mercury surface to form a layer in contact with the surface of said mercury, and continuously withdrawing said water from said container, whereby to replace the water of said layer with freshly oxygenated water, at such a rate as to maintain therein the desired oxygen content and to limit its contamination to acceptable levels. Preferably, said SMDE voltammetric cell is basically the cell described in said PCT application WO 96/35117 as well as in PCT application WO 96/35118, with which the mercury purification means of this invention are combined. In this case, said inlet into the cell is the inlet into the deoxygenating means. However, this invention can be carried out with voltammetric cells other than those described in said PCT applications, particularly cells which do not include deoxygenation means.

DETAILED DESCRIPTION OF PREFERRED EMBODIMENTS

The invention is illustrated in two embodiments as applied to an electroanalytical voltammetric cell such as described in the aforesaid PCT applications WO 96/35117 and WO 96/35118, the content of which is incorporated herein by reference, but it will be understood that it is applicable to any voltammetric cell of the dropping mercury electrode (SMDE) type, with adaptations that can be easily effected by skilled persons, insofar as any may be required.

Figure 1:
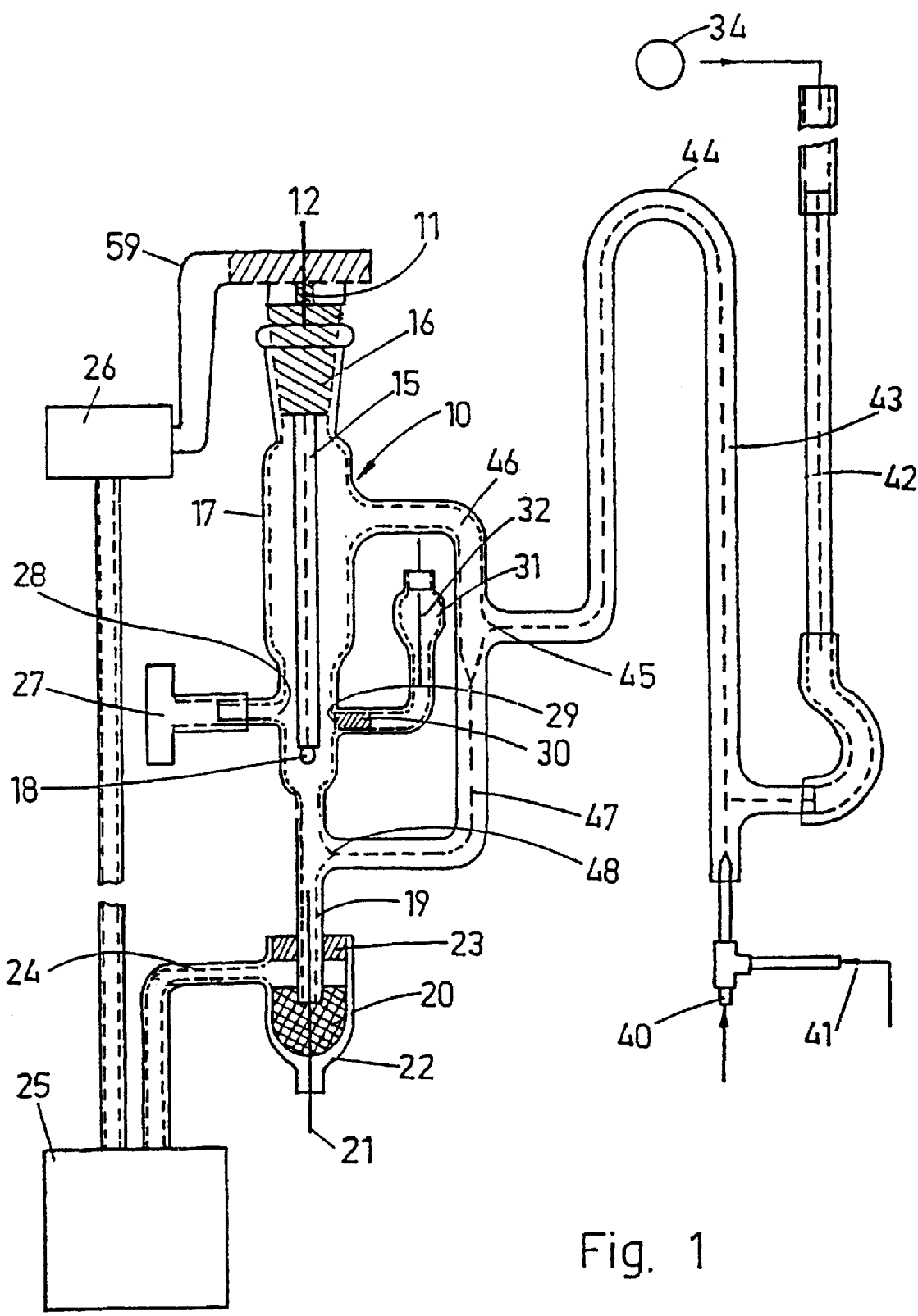
FIG. 1 is a schematic representation of a voltammetric cell according to an embodiment of the invention, seen in vertical cross-section.

FIG. 1 illustrates, in schematic vertical cross-section, an embodiment of the invention, which comprises a DME cell according to said PCT patent application WO 96/35117. The electroanalytical apparatus according to this embodiment of the invention comprises a cell proper that is generally indicated at 10. The apparatus comprises a mercury inlet 11, at the top thereof. Numeral 12 indicates a platinum wire used as an electrical contact. From inlet 11, mercury falls to capillary 15, which passes through a stopper 16 of a suitable elastic matter, preferably Teflon, which closes the top of the cell body, generally indicated at 17, said cell body being preferably made of non-absorbing material like glass or Teflon. Capillary 15 has an inner diameter equal or greater then 0.08 and preferably about 0.15 mm, which is generally large enough to avoid clogging due to solid particles or surface active materials. The working electrode is a mercury drop 18 that is formed at the end of capillary 15. Below the zone at which that drop is formed, the cell body 17 forms a pipe portion 19, which is full of sample solution. The sample solution is retained at the end of said pipe portion, because this latter sinks into a standing mercury mass 20. Said mercury mass, together with platinum wire 21, one end of which is immersed therein, constitutes the counter-electrode, and is contained in a reservoir 22, which is provided at its top with a stopper 23 through which pipe 19 passes. The reservoir 22 is connected with an outlet pipe 24. The mercury contained in the drops, which fall through pipe section 19 to reservoir 22, is added to mass 20. Concurrently, mercury overflows from reservoir 22 and is discharged through outlet 24 to a purification unit, only generally and schematically indicated at 25, which, according to an aspect of this invention, has a particular structure which will be described with reference to FIG. 2. The cell body 17 is provided with an exit 29, which is connected to a any suitable reference electrode, such as a conventional electrode or an electrode made as described in WO 96/35117. Exit 29 is closed by a porous ceramic body 30 and leads to an auxiliary vessel 31, filled with a potassium chloride solution and containing the reference electrode 32. The porous ceramic body 30 electrically connects the cell to the reference electrode by ion mobility.

The sample solution to be analyzed and which contains the electrolyte, is fed to the apparatus through inlets 40 and 41. It can be introduced into the apparatus by a peristaltic pump which feeds it to said inlets,. Through the said inlets, the solution is led into deoxygenation means. In the embodiment illustrated, this means is constituted by a conduit, indicated in this embodiment as pipe 43. Nitrogen is fed to pipe 43 through pipe 42 and other means, described hereinafter. Thus, the sample solution flows in a thin layer on the inner surface of pipe 43, while nitrogen flows centrally of said pipe; and oxygen is removed from the solution and becomes mixed with the nitrogen. Pipe 43 reaches an outlet 45 where it branches out into an upper or gas branch 46 and a lower or liquid branch 47. At the outlet 45, the sample solution becomes separated from the nitrogen stream. This latter flows upwardly through branch 46, while the sample solution flows downwardly through branch 47. The nitrogen flows into the body 17 of the cell, around mercury capillary 15, and out of it through exit 28 and pipe 27, and therefrom to the air. The sample solution enters the cell body 17 at the inlet 48, situated between the mercury drop 18 and the pipe section 19. It is trapped in said pipe section by the mercury mass 20 and fills it completely, covering platinum electrode 21 and completely filling the space between the mercury mass 20 and the mercury drops 18. It then flows upwards over the mercury capillary 15 and finally out of the cell body 17 through outlet 28 and pipe 27, and therefrom to a drain 27. Means, not shown and conventional, are provided for applying a potential between the mercury drop 18 and the reference electrode 31. Mercury flows out of reservoir 22 through pipe 24 and therefrom into container 25, in which it undergoes purification, as hereinafter explained.

In FIG. 1, a peristaltic pump, schematically indicated at 26, sucks the pure mercury from purification unit 25, and pumps it back to inlet 11 for reuse. Thus the mercury is recycled for a theoretically unlimited, and anyway very high, length of time, with no need to empty used mercury bottles or refill the mercury reservoir.

Figure 2:
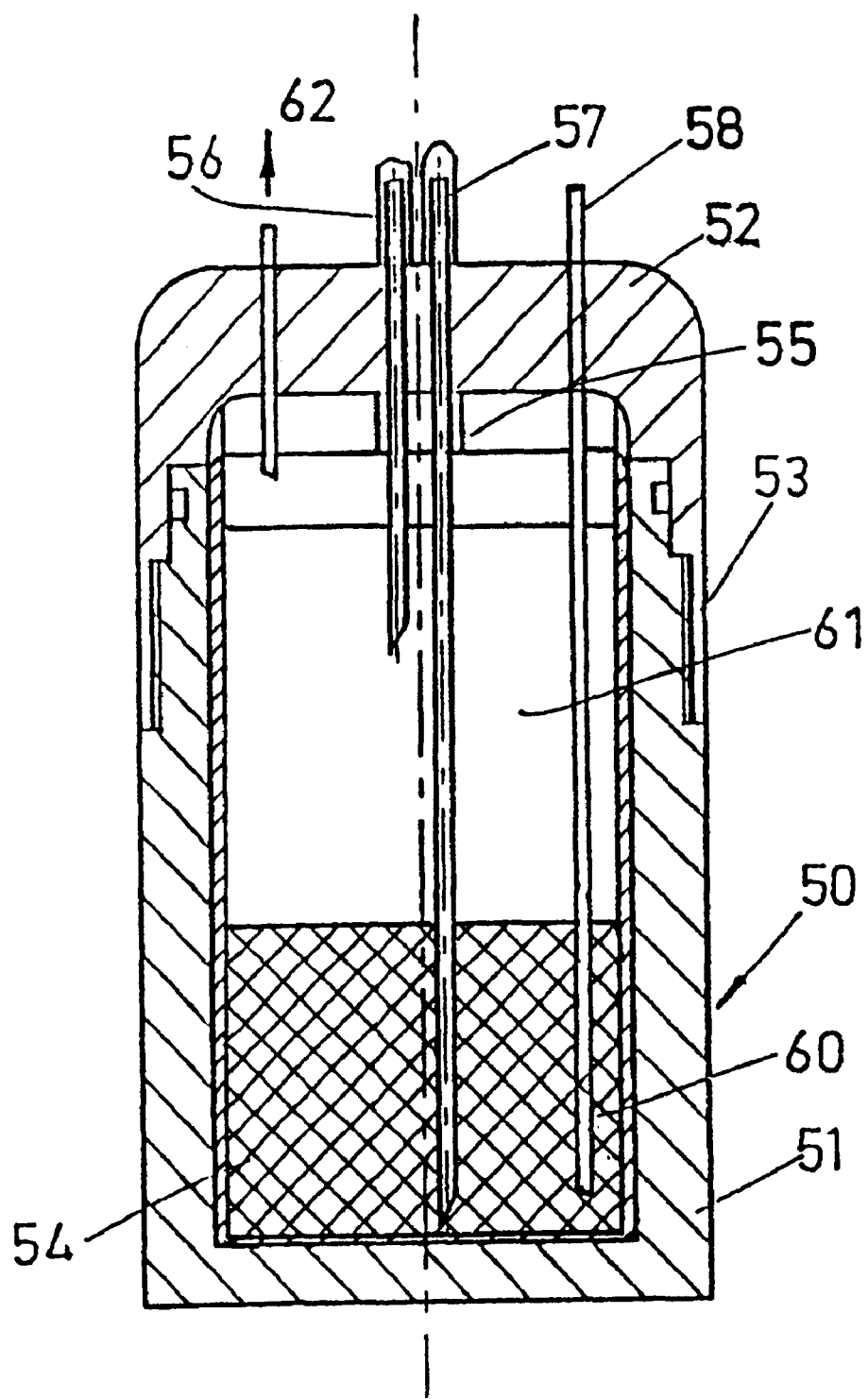
FIG. 2 is a cross-section of the mercury purification container of the embodiment of FIG. 1, shown in cross-section at an enlarged scale.

A preferred embodiment of the mercury purification unit, only generally and schematically indicated at 25 in FIG. 1, is illustrated in vertical cross-section, at a larger scale in FIG. 2 It comprises a shell 50, preferably made of plastic, consisting of a body 51 and a cap 52 that can be screwed onto it or screwed from it, as shown at 53, to permit introduction of a purification container, which is bottle 54. Bottle 54 is provided with an elastic rubber cap 55, preferably of silicon rubber, which has gas-tight passages therein for four pipes 56, 57, 58 and 62. The mercury from reservoir 20 and pipe 24 accumulates at the bottom of bottle 54 to form as mass, indicated at 60, and the upper part of the bottle contains a layer of water, preferably salty water (conductivity above 1 mS), indicated at 61. In this embodiment, the water has to be replaced when it has become excessively polluted with metals, viz. when the metal ion concentration exceeds a limit that can be easily determined in each individual case. Therefore it is preferred that the water layer be deep, so that the metal ions, diffusing out of the mercury to the water, will be diluted and the metal concentration will be low for a long period of time, whereby the water need not be replaced too often. However, this embodiment of the invention can be carried out even with a thin layer of water, e.g. having a depth of 1 cm, or even less, provided that it is replaced at shorter intervals.

In order to achieve and maintain a desired oxygen content of the water, an appropriate gas, preferably air, is bubbled, in this embodiment, through the water layer, by feeding it below the surface of the water and slightly above the level of the mercury. One way of doing this, is to feed air through pipe 58, which extends downwardly to a level close to the bottom of bottle 54, whereby the air or other oxygen containing gas, admitted through pipe 58, bubbles through the mercury and produces a mixing action, to maintain the concentration of polluting metals substantially uniform throughout the mercury mass 60. Pipe 62, which ends at a level above the surface of the water layer 61, permits the discharge of air or other oxygen containing gas that has not dissolved in the water. The contaminated mercury flows in from pipe 24 (FIG. 1), only the lowermost portion 56 of which is visible in FIG. 2, and which extends downwardly to a level close to, but below the upper surface of the water mass 61. The upper surface of the mercury mass is exposed to the oxygen dissolved in the water layer. Surprisingly the contact of the upper surface of the mercury, which mercury contains the metal impurities that it is desired to remove, with the lower surface of the oxygen containing water is sufficient to cause the metals to undergo a rapid oxidation and migrate and dissolve into the water. The oxidized and dissolved metal ions are replaced by other metal ions which migrate from the lower levels of the mercury mass to the surface and also undergo oxygenation followed by dissolution, and this process continues until the mercury is entirely purified. The pure mercury is pumped out of bottle 54 through pipe 57, which reaches to a level close to the bottom of the bottle, and is connected to pump 26, which returns the mercury back to the upper part of the cell inlet 11 through pipe 59 (see FIG. 1).

Since the oxygen content of the water in the purification container is decreased by the oxidation of the metals, and these latter become dissolved in the water and contaminate it, the water must be periodically replaced to keep the oxygen content high enough and contamination low enough.

When the operation of the voltammetric cell starts, introduction of the liquid sample into the voltammetric cell begins, and gas, in particular nitrogen, flows through the deoxygenator 43 to the cell. Once the introduction of the sample into the cell has been completed, pump 26 starts operating. As a result, the mercury flows through capillary 15 and forms drops at the lower end thereof. When the drop reaches the desired size, the pump stops running and the analysis of the sample is carried out.

Figure 3:
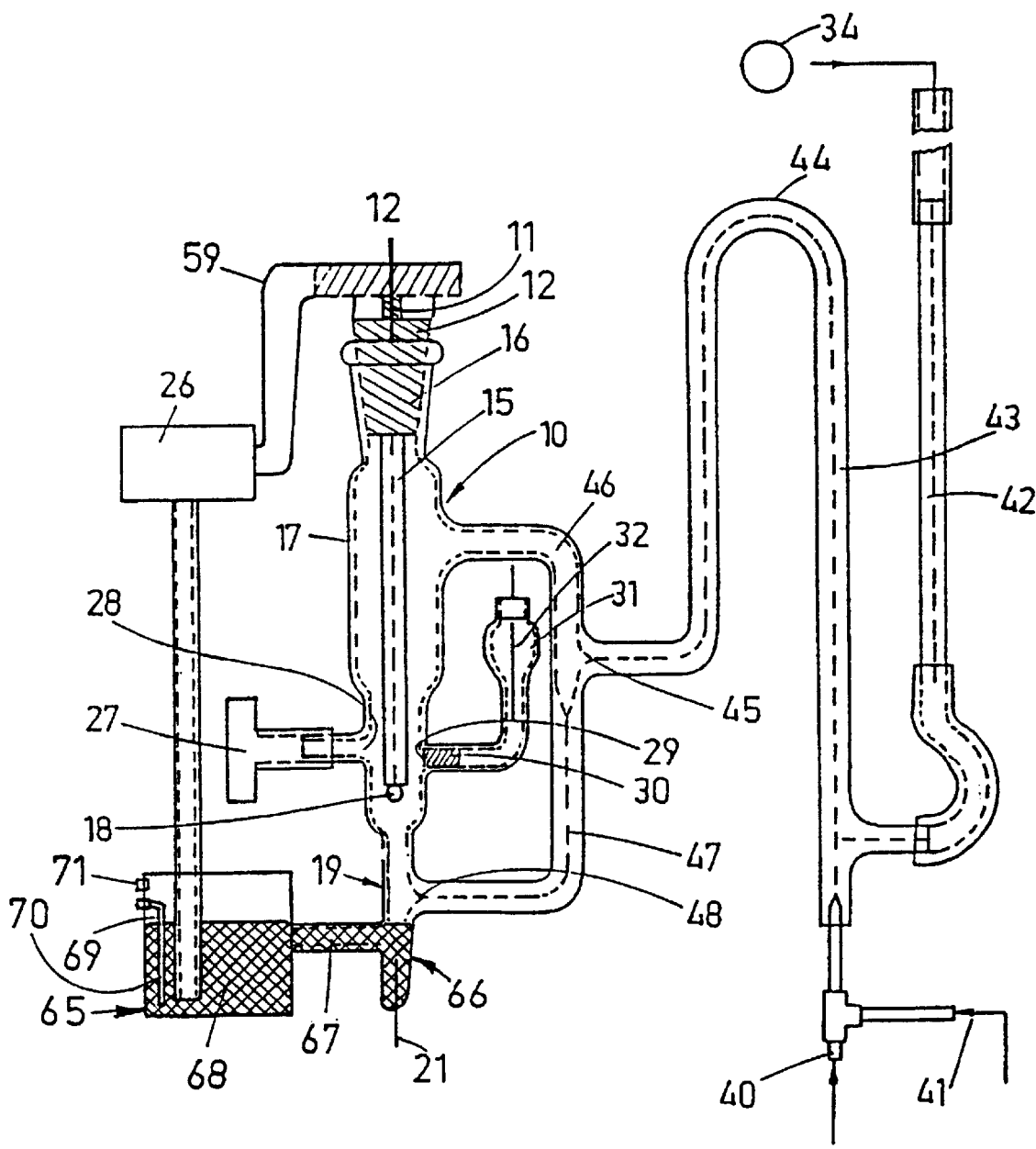
FIG. 3 illustrates, in the same way as FIG. 1, another embodiment of the invention.

In another embodiment of the invention, illustrated in FIG. 3, the voltammetric cell is the same as in FIG. 1, but the purification unit 65, which is illustrated here in schematic cross-section, has a different structure, though it is based on the same principle of oxidizing the metallic impurities In FIG. 3, the parts that are the same as in FIG. 1 are indicated by the same numerals.

In this embodiment, the working electrode is still constituted by mercury drops, formed as illustrated in FIG. 1. The fallen drops sink into a mercury trap 66 which, together with platinum wire 21, one end of which is immersed therein, constitutes the counter-electrode. The mercury is discharged from trap 66 through outlet 67 to a purification unit 65, where it forms a mass 68. Fresh, salty water (drinking water, for example) previously enriched with oxygen in any suitable way, is introduced by an inlet pipe 70 which reaches close to the bottom of the mercury mass 68, whereby to exert a mixing action to assure that the concentration of metals be substantially uniform throughout the mercury mass, and forms a layer 69 above and in contact with the upper surface of said mercury mass 68. The contact between said upper surface and the lower surface of layer 69 provides the oxidation condition necessary for the purification of the mercury, as described in connection with the purification unit 25 of FIG. 2. The water, which has lost oxygen through the oxidation process and has been contaminated by dissolved metals, is continuously withdrawn through outlet 71 above the level of inlet 70. The outlet and inlet water flow rates are, of course, equal, and are determined, for each particular cell, in such a way that the concentration of oxygen in the water remains high enough and the contamination by metals does not reach too high a level.

It is clear that, thanks to this invention, the feed of the mercury to the cell and its recovery occur without any exposure of operators to contact with the mercury, and therefore without involving any health hazards and in a completely ecological manner. Further, while embodiments of the invention, which comprise a DME cell such as described in the aforesaid PCT applications WO 96/35117 and WO 96/35118, have been described by way of example, it is clear that the invention may be applied to other DME cells, having means for feeding mercury to it and preferably recovering mercury from it.

Further, the use of a peristaltic pump for recycling the mercury, by drawing it from the purification unit and pumping it back to the working electrode, permits to stabilize the mercury drop at the tip of the capillary tube after it reaches the desired size, viz. to produce a static drop. Thanks to the longer lifetime of the drop, the device according to the invention is adapted to apply improved electroanalytic techniques, such as anodic stripping techniques. Further, the ability to stabilize the drop enables the use of larger capillary tubes, e.g. up to 200 μm, thus reducing the sensitivity of the apparatus to small diameter particles; and in the event that a particle penetrates the tube, it is forced out by the pump which drives the mercury through the tube.

An important parameter, in the process of this invention, is the ratio between the concentration of metal ions at the surface of the mercury and their concentration in the bulk of the water. Such a ratio should preferably be at least 1:100, viz. the metal concentration in the water bulk should be 100 times or more lower than the concentration at the mercury surface. It will also be apparent that the invention can be carried out by persons skilled in the art with many modifications, variations and adaptations, without departing from its spirit or exceeding the scope of the claims.

What is claimed is:

1. Electroanalytical apparatus, which comprises a Static Mercury Drop Electrode cell, said cell comprising a capillary tube at the end of which are formed mercury drops that constitute the working electrode, said apparatus further comprising; a container for continuously receiving and collecting mercury that has formed said working electrode and has become contaminated, a purifying vessel in a fixed relationship to said capillary tube, conduit means for continuously bringing collected mercury from said container into said purifying vessel, means for bringing highly oxygenated water into said purifying vessel at a location above the mercury collected in said vessel such that surface contact is established between said highly oxygenated water and the mercury collected in the purifying vessel, and means for continuously drawing mercury from said purifying vessel and feeding it as purified mercury to said capillary tube, wherein said mercury accumulating in said purification vessel forms a mercury mass having an upper surface, and means for forming a layer of highly oxygenated water in said container above said mercury mass, said layer having a lower surface in contact with said upper surface of said mercury mass, wherein the means for forming a layer of highly oxygenated water in the purification vessel above the mercury mass further comprises means for bubbling oxygen or an oxygen containing gas through said layer above the mercury mass.

2. Apparatus according to claim 1, wherein the means for bubbling oxygen or oxygen containing gas through the mercury mass creates a mixing action to maintain the concentration of contaminants uniform throughout said mercury mass.

3. Electroanalytical apparatus, which comprises a Static Mercury Drop Electrode cell, said cell comprising a capillary tube at the end of which are formed mercury drops that constitute the working electrode, said apparatus further comprising; a container for continuously receiving and collecting mercury that has formed said working electrode and has become contaminated, a purifying vessel in a fixed relationship to said capillary tube, conduit means for continuously bringing collected mercury from said container into said purifying vessel, means for bringing highly oxygenated water into said purifying vessel at a location above the mercury collected in said vessel such that surface contact is established between said highly oxygenated water and the mercury collected in the purifying vessel, and means for continuously drawing mercury from said purifying vessel and feeding it as purified mercury to said capillary tube, wherein said apparatus further comprises first pipe means for introducing into said purification vessel contaminated mercury to form a mercury mass, second pipe means for bubbling oxygen or an oxygen containing gas through a layer of water superimposed to said mercury mass and through the mercury mass, third pipe means in communication with a suction pump for drawing purified mercury from said mercury mass, and fourth pipe means for discharging undissolved gas.

* * * * *